United States Patent
Klein et al.

(10) Patent No.: US 6,835,839 B2
(45) Date of Patent: Dec. 28, 2004

(54) METHOD FOR THE PRODUCTION OF BIPERIDEN II

(75) Inventors: Peter Klein, Waldstrasse (DE); Marco Thyes, Mendelssohnstrrasse (DE); Markus Grosse, Ludwigsh (DE); Klaus Martin Weber, Rottstrasse (DE); Elmar Vilsmaier, Otterbach (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 10/477,766

(22) PCT Filed: May 17, 2002

(86) PCT No.: PCT/EP02/05500
§ 371 (c)(1),
(2), (4) Date: Apr. 5, 2004

(87) PCT Pub. No.: WO02/094781
PCT Pub. Date: Nov. 28, 2002

(65) Prior Publication Data
US 2004/0152899 A1 Aug. 5, 2004

(30) Foreign Application Priority Data
May 18, 2001 (DE) ......................... 101 24 449

(51) Int. Cl.[7] ............................................ C07D 211/06
(52) U.S. Cl. ..................................................... 546/205
(58) Field of Search .......................................... 546/205

(56) References Cited

U.S. PATENT DOCUMENTS 2,789,110 A 4/1957 Wilfrid

FOREIGN PATENT DOCUMENTS

| DE | 10 05 067 B | 3/1957 |
| JP | 11189729 A | 7/1999 |
| WO | WO 02/094781 A1 | 5/2002 |

OTHER PUBLICATIONS

Ronald Breslow and Uday Maitra, On the Origin of Product Selectivity in Aqueous Dies–Alder Reactions, Tetrahedron Letters. vol. 25. No. 12, pp 1239–1240, 1984, Great Britain.
Ullmans Enzykopadie der technischen Chemie, 4 Aufl., vol. 21, Verlag Chemie, 1982, p. 627.
J. G. Dinwiddie and S. P. McManus (J. Org. Chem., 1965, 30, 766).
Eltze et al, Eur. J. of Pharmacology, vol. 158, p. 11–19 (1988).

*Primary Examiner*—Bernard Dentz
(74) *Attorney, Agent, or Firm*—Wood, Phillips, Katz, Clark & Mortimer

(57) ABSTRACT

The invention relates to a method for the production of biperiden by reacting an exo/endo mixture of 1-(bicyclo [2.2.1.]hept-5-en-2-yl) 3-piperidino-1-propanone with a phenyl magnesium compound, wherein the exo/endo ratio of 1-(bicylo[2.2.1]hept-5-en-2-yl)-3-piperidino-1-propanone is at least 4.5:1.

15 Claims, No Drawings

METHOD FOR THE PRODUCTION OF BIPERIDEN II

This application is a 371 of PCT/EP02/05500 filed May 17, 2002.

The present invention relates to a method for the production of biperiden.

Biperiden is a well-known central anticholinergic agent and is employed for the treatment of Parkinson's disease (Ullmanns Enzyklopädie der technischen Chemie, 4th edition, volume 21, Verlag Chemie, 1982, p. 627). It comprises a racemate of 1-(bicyclo[2.2.1]hept-5-en-2-yl(exo, R))-1-phenyl-3-piperidinopropanol (1,S) and 1-(bicyclo[2.2.1]hept-5-en-2-yl(exo,S))-1-phenyl-3-piperidinopropanol(1,R) (Ia) and represents one of four possible pairs of enantiomers (Ia-d) of the amino alcohol 1-(bicyclo[2.2.1]hept-5-en-2-yl)-1-phenyl-3-piperidino-1-propanol (I).

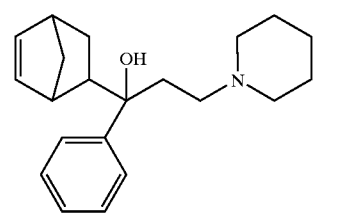

(I)

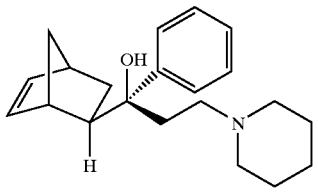

(exo, R)/(1, S)

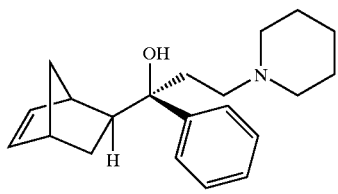

(exo, S)/(1, R)

(Ia)

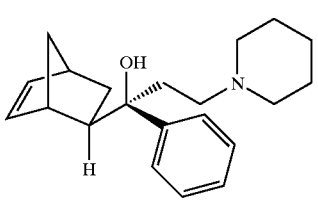

(exo, R)/(1, R)

(Ib)

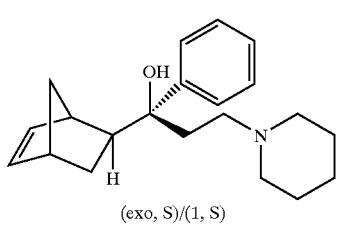

(exo, S)/(1, S)

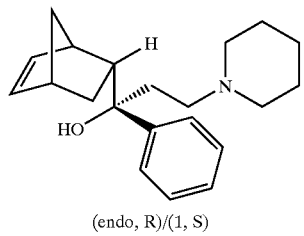

(endo, R)/(1, S)

(Ic)

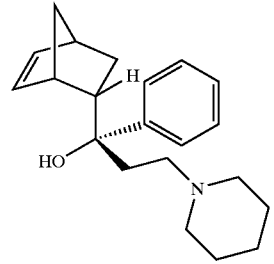

(endo, S)/(1, R)

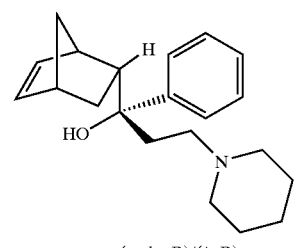

(endo, R)/(1, R)

(Id)

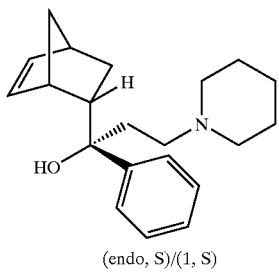

(endo, S)/(1, S)

DE 1 005 067 and U.S. Pat. No. 2,789,110 describe the preparation of the amino alcohol I by reacting 1-(bicyclo[2.2.1]hept-5-en-2-yl)-3-piperidino-1-propanone (II) with a phenylmagnesium halide. U.S. Pat. No. 2,789,110 additionally describes the preparation of the propanone II starting from 1-(bicyclo[2.2.1]hept-5-en-2-yl)-ethanone (III), paraformaldehyde and piperidine hydrochloride in a Mannich reaction, and the preparation of the ethanone III from cyclopentadiene and methyl vinyl ketone in a Diels-Alder cycloaddition.

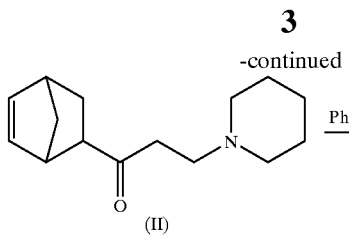

Neither DE 1 005 067 nor U.S. Pat. No. 2,789,110 disclose whether the amino alcohol I obtained in this way is a mixture of isomers or a pure isomer.

The precursor for preparing the propanol, 1-(bicyclo[2.2.1]hept-5-en-2-yl)-3-piperidino-1-propanone (II), can exist in two isomeric forms, as exo or as endo isomer (II-exo, II-endo), and only the exo form is able to afford biperiden in the abovementioned reaction with a phenylmagnesium halide.

(II)

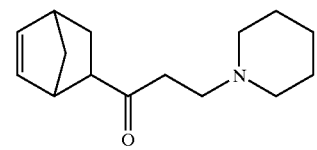

(II-exo)

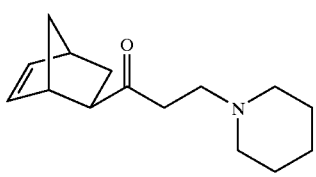

(II-endo)

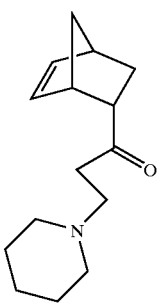

The structural formulae of II-exo and of II-endo show for the sake of simplicity in each case only one of two possible enantiomers of the exo isomer and endo isomer, respectively. However, the designation II-exo or II-endo relates hereinafter to the pair of enantiomers of the exo or endo form.

1-(Bicyclo[2.2.1]hept-5-en-2-yl)ethanone (III), the starting substance for synthesizing the propanone II, may also exist both as exo and as endo isomer (III-exo, III-endo) and, correspondingly, only reaction of the exo isomer leads in the subsequent steps to biperiden.

(III-exo)

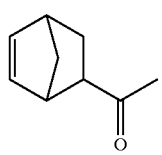

(III)

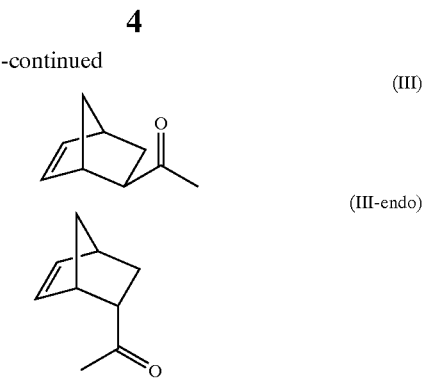

(III-endo)

The structural formulae of III-exo and of III-endo show for the sake of simplicity in each case only one of two possible enantiomers of the exo isomer and endo isomer, respectively. However, the designation III-exo or III-endo relates hereinafter to the pair of enantiomers of the exo or endo form.

It is not possible to infer any information about the configuration of the precursors III and intermediates II employed in any of the abovementioned publications.

It is known that 1-(bicyclo[2.2.1]hept-5-en-2-yl)ethanone (III) is obtained from the cycloaddition in an exo/endo ratio of 1:4 (e.g. R. Breslow, U. Maitra, Tetrahedron Letters, 1984, 25, 1239). Since the prior art mentioned at the outset makes no statements at all about the stereochemistry of the ethanone III, it must be assumed that the ethanone III was employed in this ratio of isomers to prepare the amino alcohol I.

The preparation of exo-1-(bicyclo[2.2.1]hept-5-en-2-yl)ethanone (III-exo) was described in 1965 by J. G. Dinwiddie and S. P. McManus (J. Org. Chem., 1965, 30, 766). This entails exo/endo mixtures of 1-(bicyclo[2.2.1]hept-5-en-2-yl)ethanone (III) in which the endo content predominates being heated in methanol in the presence of sodium methanolate and isomerizing to mixtures with an exo content of about 70%. It is possible to obtain from this by fractional distillation and, where appropriate, redistillation of the distillate exo-1-(bicyclo[2.2.1]hept-5-en-2-yl)ethanone (III-exo) with a purity of up to 95%.

Experiments by the applicant have shown that even on use of virtually pure exo ethanone III-exo, i.e. of an ethanone III with an exo content of at least 95%, as starting material of the Mannich reaction an exo/endo mixture of propanone II having a maximum exo/endo ratio of 4.0:1 is always obtained. This is unsatisfactory as regards obtaining pure biperiden (Ia) from reaction of the propanone II with a phenylmagnesium compound. Pure biperiden means a biperiden (Ia) with a purity of at least 99.0%, as is generally necessary for pharmaceutical applications.

It is an object of the present invention to provide a method for the production of biperiden, which provides the latter in higher yield. The meaning of biperiden is a substance of the structural formula Ia. It is particularly intended to improve the selectivity of the propanone II production in relation to the exo isomer.

We have found that this object is achieved by a method for the production of biperiden by reacting an exo/endo mixture of 1-(bicyclo[2.2.1]hept-5-en-2-yl)-3-piperidin-1-propanone (II) with an exo/endo ratio of at least 4.5:1 with a phenylmagnesium compound, characterized in that the production of the exo/endo mixture of 1-(bicyclo[2.2.1]hept-5-en-2-yl)-3-piperidino-1-propanone (II) comprises the following steps:

a) reaction of exo-1-(bicyclo[2.2.1]hept-5-en-2-yl)ethanone (III-exo) with a formaldehyde source and an acid addition salt of piperidine or with a formaldehyde source and piperidine in the presence of an acid in an organic solvent or in a mixture thereof with water, b) conversion of the resulting reaction mixture into an aqueous solution and extraction of this aqueous solution with an organic solvent which has limited miscibility or is immiscible with water at a pH not exceeding 7, and c) extraction of the raffinate obtained in b), which contains the exo/endo mixture of 1-(bicyclo[2.2.1]hept-5-en-2-yl)-3-piperidino-1-propanone (II), at a pH of at least 7.5 with an organic solvent which has limited miscibility or is immiscible with water, d) removal of the organic extract, purification of the organic extract by extraction with aqueous acid and subsequent removal of the solvent, resulting in 1-(bicyclo-[2.2.1]hept-5-en-2-yl)-3-piperidino-1-propanone (II) with an exo/endo ratio of at least 4.5:1.

The meaning of exo-1-(bicyclo[2.2.1]hept-5-en-2-yl) ethanone (III-exo) hereinafter is an ethanone III with an exo content of at least 96%.

The exo and endo isomers employed in the method of the invention comprise, as already described for the exo and endo ethanone III-exo and III-endo and for the exo and endo propanone II-exo and II-endo, pairs of enantiomers. In order to obtain biperiden (Ia), which is itself a racemate, racemic mixtures of enantiomers of the starting materials and of the intermediates are employed. However, the method of the invention can also be applied to pure enantiomers and to non-racemic mixtures of enantiomers.

Reaction of exo-1-(bicyclo-[2.2.1]hept-5-en-2-yl) ethanone (III-exo) with a Mannich reaction with a formaldehyde source and an acid addition salt of piperidine or with a formaldehyde source and piperidine in the presence of an acid generally takes place in a solvent suitable for Mannich reactions. Suitable solvents are, in particular, $C_1$–$C_4$-alkanols, e.g. methanol, ethanol, n-propanol, isopropanol, sec-butanol or isobutanol, and mixtures thereof with water. Isopropanol is preferably used.

Suitable acids are in principle the mineral acids or organic acids suitable for Mannich aminomethylation.

Hydrochoric acid or hydrogen chloride or an organic sulfonic acid of the general formula $RSO_3H$ is preferably used. R in this case is a monovalent organic radical, preferably $C_1$–$C_4$-alkyl, phenyl or $C_1$–$C_4$-alkyl-substituted phenyl, with methyl being particularly preferred. The reaction can take place with the acid addition salt of piperidine or else with piperidine in the presence of an acid, in which case the acid addition salt of piperidine is formed in situ.

In this case, piperidine and the appropriate acid are preferably employed in equimolar amounts. In the case where the isolated acid addition salt of piperidine is used, if the latter cannot be purchased commercially it can be prepared by reaction of piperidine with an appropriate acid in molar ratios in the range from 1:0.9 to 1:2, preferably in the range from 1:0.9 to 1:1.5, in particular in the range from 1:0.9 to 1:1.2 and particularly preferably approximately equimolar and by a subsequent isolation.

The isolated acid addition salt of piperidine is preferably employed in the Mannich reaction. Piperidine hydrochloride or piperidinium methanesulfonate is particularly preferably employed.

The exo ethanone III-exo and the formaldehyde source are preferably employed in a molar ratio of from 1:1 to 1:2, the formaldehyde source being employed in particular in an excess of from 10 to 100 mol % and particularly preferably from 10 to 30 mol %, e.g. 20 mol %. Gaseous formaldehyde, formalin, trioxane or paraformaldehyde are suitable as formaldehyde source. Paraformaldehyde is preferably used.

The exo ethanone III-exo and piperidine or the acid addition salt of piperidine are preferably employed in a molar ratio of from 1:0.9 to 1:2, in particular from 1:0.95 to 1:1.5 and particularly preferably from 1:1 to 1:1.3.

When hydrochloric acid or hydrogen chloride is used as acid, the exo ethanone III-exo and piperidine or its acid addition salt are reacted in a molar ratio in the range from 1:0.9 to 1:1.5, preferably in the range from 1:0.9 to 1:1.2 and particularly preferably approximately equimolar. In a special embodiment, the molar ratios of the components exo ethanone III-exo, piperidine or its acid addition salt and formaldehyde source are 1:1–1.01:1.2.

When a sulfonic acid is used, the exo ethanone III-exo and piperidine or its acid addition salt are usually employed in a molar ratio in the range from 1:1 to 1:2. Piperidine or its acid addition salt is preferably employed in excess, preferably using an excess of from 10 to 100 mol %, particularly preferably from 10 to 30 mol %, e.g. 20 mol %. Piperidine or its acid addition salt and the formaldehyde source are in this case suitably employed in a molar ratio in the range from 1:0.9 to 1:1.2, preferably approximately equimolar. In a special embodiment, the molar ratios of the components exo ethanone III-exo, piperidine or its acid addition salt and formaldehyde source are 1:1.2:1.2.

The reaction temperature for the Mannich reaction is usually in the range from 0° C. to the boiling point of the reaction mixture. Heating to reflux is preferred. The reaction usually takes from 2 to 24 hours, preferably 5 to 12 hours and particularly preferably from 5 to 8 hours.

The conversion of the reaction mixture obtained in step a) usually takes place in such a way that firstly the organic solvent is removed from the reaction mixture, which is normally carried out by distillation, preferably under reduced pressure. The residue is then taken up where necessary in water, i.e. when a solid or oily residue is obtained. If an aqueous mixture is obtained, this can be diluted with water where appropriate. The aqueous mixtures obtained in this way are extracted one or more times to remove non-basic organic constituents—usually unreacted starting material—with an organic solvent which has limited miscibility or is immiscible with water, with the pH of the aqueous phase not exceeding a value of 7.0. Suitable solvents which have limited miscibility or are immiscible with water include $C_5$–$C_8$-aliphatic compounds such as n-pentane or n-hexane, $C_5$–$C_6$-alicyclic compounds such as cyclohexane, aromatic compounds such as benzene, toluene or xylenes and aliphatic $C_4$–$C_8$-ethers such as diethyl ether, tert-butyl methyl ether or diisopropyl ether, or mixtures thereof. Aliphatic $C_4$–$C_8$-ethers, in particular diisopropyl ether, are preferably used for the extraction.

The procedure for this is preferably such that firstly the aqueous [lacuna] which is usually still acidic is extracted with the water-immiscible solvent. The aqueous mixture is preferably extracted more than once, in particular 2 to 5 times and specifically 3 times.

The pH of the raffinate can then be raised with a base, maintaining at $\leq 7$, followed by extraction. This procedure is preferred. For this purpose, the aqueous solution is preferably treated one or more times with a mixture of a base or of an aqueous basic solution and one or more of the abovementioned solvents suitable for extracting the aqueous phase, preferably diisopropyl ether. The bases normally used are alkali metal or alkaline earth metal hydroxides or alkali metal carbonates. Sodium hydroxide or potassium hydroxide or aqueous solutions thereof are preferably used, in particular sodium hydroxide or sodium hydroxided solution. The total amount of base employed is in the range from 5 to 15 mol %, preferably 8 to 10 mol %, relative to the amount of exo ethanone III-exo employed. The pH of the aqueous phase should not exceed pH 7 during this.

The aqueous solution is then adjusted in step c) of the method of the invention in one or more stages with one of the abovementioned bases or an aqueous basic solution, preferably sodium hydroxide or sodium hydroxide solution, to a pH of at least 7.5, preferably in the range from 7.5 to 9, in particular in the range from 8 to 8.5 and particularly preferably in the range from 8.1 to 8.3. In the stepwise basification of the aqueous phase, each addition of the base or of the aqueous basic solution is followed by extraction of the aqueous solution suitably with one of the abovementioned organic solvents suitable for extracting the aqueous phase, preferably diisopropyl ether; with one-stage addition of the base or of the aqueous basic solution, this correspondingly takes place subsequent thereto, in this case extracting where appropriate more than once, e.g. three to five times, with the organic solvent.

The organic extracts, which contain the 1-(bicyclo[2.2.1]hept-5-en-2-yl)-3-piperidino-1-propanone (II), are usually combined and purified in step d) by extraction with acid. For this purpose, the organic extract obtained in step c) is usually treated with an aqueous, in particular a dilute aqueous, acid. This can, where appropriate, be followed by washing with water. Mineral acids such as hydrochloric acid, hydrobromic acid, sulfuric acid or phosphoric acid are generally used as acid, and hydrochloric acid is preferably used. The amount of acid employed is usually from 0.02 to 0.10 proton equivalent, preferably 0.03 to 0.05 proton equivalent, of the amount of exo ethanone III-exo employed in the Mannich reaction. Proton equivalents mean the number of protons in an acid molecule. The concentration of the aqueous acid is usually in the range form 0.5 to 10 M and in particular in the range from 2 to 7 M.

The organic extract is then freed of solvent, which preferably takes place in vacuo.

The residue remaining after removal of the solvent by evaporation, which consists of at least 95% by weight of the exo/endo mixture of the propanone II, contains the latter in an exo/endo ratio of at least 4.5:1, in particular of at least 6:1, and in the case where piperidinium methanesulfonate is used as starting material in the Mannich reaction of at least 10:1, in particular of at least 15:1, e.g. of 22:1.

The exo/endo mixture of the propanone II obtained after the workup of the invention contains the exo propanone II-exo in a considerably greater proportion than the exo/endo mixture of the propanone II obtained after the usual workup by distillation, while the overall yield of exo/endo propanone II is at least equally large.

The exo/endo mixture of 1-(bicyclo[2.2.1]hept-5-en-2-yl)-3-piperidino-1-propanone (II) produced according to the invention is reacted in a Grignard reaction in a suitable solvent with a phenylmagnesium compound, preferably with diphenylmagnesium or particularly preferably with a phenylmagnesium compound of the general formula

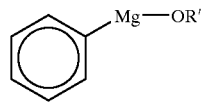

in which R' is $C_1$–$C_4$-alkyl such as methyl, ethyl, n-propyl, isopropyl or n-butyl, $C_4$–$C_6$-cycloalkyl such as cyclohexyl, $C_4$–$C_6$-cycloalkyl-$C_1$–$C_4$-alkyl such as 2-cyclohexylethyl, phenyl-$C_1$–$C_4$-alkyl such as benzyl, 2-phenylethyl or 3-phenylpropyl, substituted phenyl-$C_1$–$C_4$-alkyl such as 3,4-(methylenedioxy)benzyl, heteroaryl such as 8-quinolyl, heteroaryl-$C_1$–$C_4$-alkyl such as furfuryl, 2-thienylmethyl or 2-(2-thienyl)ethyl, or benzhydryl. The phenylmagnesium compound of the formula depicted above is referred to below as phenylmagnesium alkoxide.

Suitable solvents are aromatic compounds such as benzene, toluene, or xylenes, acyclic or cyclic ethers having 4 to 6 C atoms, mixtures thereof or mixtures of them with aliphatic or alicyclic hydrocarbons such as n-hexane or cyclohexane. Examples of suitable alicyclic ethers are diethyl ether and tert-butyl methyl ether, and examples of suitable cyclic ethers are tetrahydrofuran and dioxane. Diethyl ether, tetrahydrofuran or dioxane or mixtures thereof are preferably used. The solvents are usually employed anhydrous, as normal for Grignard reactions.

The phenylmagnesium alkoxide is prepared in a generally known manner, e.g. by reacting diphenylmagnesium with an alcohol of the general formula R' OH in which R' is as defined above. Diphenyl-magnesium and the alcohol are for this purpose reacted in a molar ratio in the range from 1:0.9 to 1:1.5, preferably in the range from 1:1 to 1:1.2 and particularly preferably approximately equimolar. Diphenylmagnesium, which is usually generated in situ as described hereinafter, is ordinarily introduced into one of the abovementioned solvents suitable for Grignard reactions, and the alcohol is normally added in portions over a period of from 5 minutes up to about one hour at a temperature of from 0 to 80° C., preferably from 0 to 50° C. and particularly preferably from 0 to 40° C. After the addition is complete, the mixture can be left, or preferably stirred, in the same temperature range for 15 minutes to 2 hours, preferably 15 minutes to one hour, until the reaction is complete.

The diphenylmagnesium employed in the method of the invention is produced in a manner known per se. For example, dioxane can be added to a phenylmagnesium halide, e.g. phenylmagnesium chloride, in a suitable solvent, thus shifting the Schlenk equilibrium to result in diphenylmagnesium and the corresponding magnesium halide-dioxane complex. The latter usually precipitates, but is preferably not removed from the solution. Suitable solvents are generally acyclic and cyclic ethers preferably having 4 to 6 C atoms or mixtures thereof with aliphatic, alicyclic or aromatic hydrocarbons. Examples of suitable acyclic ethers are diethyl ether and tert-butyl methyl ether, and a suitable cyclic ether is tetrahydrofuran. The suitable aliphatic and alicyclic hydrocarbons include in particular n-hexane and cyclohexane, and examples of suitable aromatic hydrocarbons are benzene, toluene and xylenes.

Dioxane is ordinarily employed at least equimolar in relation to the phenylmagnesium halide. If diphenylmagnesium is to be used as phenylmagnesium compound, then dioxane is preferably employed in excess, for example in an excess of from 50 to 500 mol %, in particular from 100 to 300 mol % and specifically of from 100 to 200 mol %. If diphenylmagnesium is first to be converted into the phenylmagnesium alkoxide, preferably dioxane and the phenylmagnesium halide are employed in a molar ratio in the range from 1:1 to 1.5:1, in particular 1:1 to 1.2:1 and particularly preferably approximately equimolar.

The dioxane is added to the solution of the phenylmagnesium halide usually at a temperature in the range from −20 to 60° C., preferably in the range from −10 to 40° C.

The mixture obtained after addition of the dioxane is normally left for from 15 minutes to 2 hours, preferably 20 minutes to one hour, in the temperature range mentioned for the addition of the dioxane, before it is employed in the method of the invention.

Both the preparation of diphenylmagnesium, the reaction to give the phenylmagnesium alkoxide and the Grignard reaction of the phenylmagnesium compound with the propanone II are suitably carried out under an inert gas atmosphere. Examples of suitable inert gases are nitrogen and the noble gases such as argon, and mixtures thereof.

In the Grignard reaction of the propanone II with the phenyl-magnesium compound, ordinarily the phenylmagnesium compound and the propanol II are employed in a molar ratio in the range from 0.8:1 to 3:1, preferably from 0.8:1 to 2:1 and in particular from 0.8:1 to 1.5:1. Where diphenylmagnesium or the phenylmagnesium alkoxide is used, the phenylmagnesium compound and the propanone II are particularly preferably employed in a molar ratio in the range from 1:1 to 1.3:1.

Ordinarily, the propanone II is added to the phenylmagnesium compound in the form of a solution in one of the abovementioned organic solvents suitable for Grignard reactions at a temperature in the range from $-20°$ C. to the boiling point of the reaction mixture, preferably in the range from $-10°$ to $90°$ C. and particularly preferably in the range from $0°$ C. to $70°$ C. The phenylmagnesium compound is moreover ordinarily employed in a concentration in the range from 0.1 to 10 mol/l, preferably in the range from 0.1 to 3 mol/l and particularly preferably in the range from 0.2 to 2 mol/l.

The propanone II can be added in one portion or, preferably, over a period of from a few minutes up to several hours, e.g. 5 minutes to 5 hours. The propanone II is added either in the form of a solution in one of the abovementioned inert solvents suitable for Grignard reactions or, preferably, in pure form. When added as solution, the concentration of the propanone II is ordinarily from 0.1 to 20 mol/l, preferably 1 to 15 mol/l. To complete the reaction, the reaction mixture is normally left at a temperature in the range from $-20°$ C. to the boiling point of the reaction mixture, preferably in the range from $-10°$ C. to $90°$ C. and particularly preferably in the range from $10°$ C. to $80°$ C. for from 15 minutes to 5 hours, specifically 30 minutes to 2 hours, during which it is preferably stirred to improve mixing. Workup is, as usual for Grignard reactions, by aqueous extraction, e.g. by quenching the reaction mixture with water, an aqueous ammonium chloride solution or an acidic aqueous solution, with the pH of the resulting mixture in the latter case subsequently being made alkaline, extracting the quenched mixture, where appropriate after removal of an organic phase, with a water-immiscible solvent suitable for dissolving the product, and removing the solvent from the extract or from the extract combined with the organic phase. Examples of suitable solvents are aromatic compounds such as benzene or toluene, the abovementioned acyclic ethers, esters such as ethyl acetate or chlorine-containing aliphatic compounds such as dichloromethane or trichloromethane.

The crude product obtained from the reaction of the propanone II with diphenylmagnesium or with the phenylmagnesium alkoxide consists essentially of the four diastereomeric pairs of enantiomers Ia to Id of 1-(bicyclo[2.2.1]hept-5-en-2-yl)-1-phenyl-3-piperidino-1-propanol (I), with the pair of enantiomers Ia (biperiden) forming the major quantity. The ratio of biperiden (Ia) to the other three pairs of enantiomers Ib to Id determined by gas chromatography is normally at least 1.5:1 and is preferably in the range from 1.7:1 to 2.4:1. Particularly high proportions of the pair of enantiomers Ia are obtained for example when diphenylmagnesium or phenylmagnesium benzyl alcoholate is reacted with the propanone II which has been obtained from the reaction of the exo ethanone III-exo with piperidinium methanesulfonate.

The biperiden (Ia) is isolated from the mixture of diastereomers by dissolving the latter with heating, preferably at a temperature of from 40 to $80°$ C., in particular from 50 to $70°$ C., in a mixture of water and a polar, water-miscible organic solvent.

Suitable solvents are $C_1$–$C_3$-alkanols, i.e. methanol, ethanol, n-propanol and isopropanol. Aqueous isopropanol is preferably used, particularly preferably 70 to 95% isopropanol and especially 90% isopropanol. The percentage data given here and hereinafter in relation to the isopropanol content are based on the volume of the isopropanol relative to the total volume of the water-containing solvent. HCl is added to this solution, for example in the form of a solution of hydrogen chloride in an organic solvent, preferably in one of the $C_1$–$C_3$-alkanols mentioned, with preference in isopropanol, or in the form of hydrochloric acid. HCl is employed at least equimolar in relation to the amino alcohol I, preferably in an excess of from 5 to 50 mol % and particularly preferably from 5 to 20 mol %. The addition preferably takes place at elevated temperature, e.g. at 40 to $80°$ C. and in particular at 50 to $70°$ C. To complete the reaction after addition is complete, the reaction mixture is left at a temperature of from $50°$ C. up to the boiling point of the reaction mixture for 0.5 to 3 hours, preferably while stirring. In a preferred embodiment, the reaction mixture is stirred at 55 to $65°$ C. for the first two thirds of the time and then stirred at the reflux temperature for one third of the time. The reaction mixture is then cooled to a temperature in the range from 0 to $30°$ C., where appropriate stirred in this temperature range for up to several hours, e.g. up to 10 hours, preferably up to 5 hours, and then the hydrochloride which has formed is removed from the solution in a conventional way.

For further purification of the hydrochloride, it is generally taken up wet or dry in water and a sufficient amount of one or more polar dialkyl ethers of limited or zero miscibility with water and having 4 to 8 C atoms, such as diethyl ether, tert-butyl methyl ether and especially diisopropyl ether, and a suitable base is added to the mixture. Suitable amounts of organic solvents are, for example, from 4 to 10 ml of solvent per gram of dry hydrochloride. Water and organic solvent are preferably employed in a ratio in the range from 1:2 to 1:5 by volume.

Suitable bases are alkali metal and alkaline earth metal hydroxides, and alkali metal carbonates; sodium or potassium hydroxide or their aqueous solutions are particularly preferably used, sodium hydroxide or sodium hydroxide solution are especially used. However, it is also possible to use water-soluble organic bases, for example amines having aliphatic substituents and 2 to 8 C atoms. The base is employed at least equimolar, preferably in excess, in particular in an excess of from 5 to 15 mol % based on the hydrochloride.

The reaction with the base preferably takes place at elevated temperature. For this purpose, before, during or, preferably, after addition of the base the mixture is heated to a temperature in the range of $25°$ C. up to the boiling point of the reaction mixture, preferably in the range from 30 to $70°$ C., and when diisopropyl ether is used as dialkyl ether preferably in the range from 40 to $65°$ C., in particular from 55 to $60°$ C. This generally results in two clear phases which are separated at elevated temperature, in the case where diisopropyl ether is used as dialkyl ether in the abovementioned temperature range. The organic phase is washed with water at elevated temperature, in the case where diisopropyl ether is used as dialkyl ether in the abovementioned temperature range, and then concentrated preferably under atmospheric pressure by removing the solvent until the weight/volume ratio of the product to the solvent is in the range from 1:2 to 1:6, preferably from 1:3 to 1:4.5. When the mixture is cooled to room temperature or below, but preferably not below −10° C., pure biperiden (Ia) crystallizes out and is isolated by conventional methods for isolating solids, e.g. filtering off the solid or decanting off the mother liquor.

It was possible by the use according to the invention of the propanone II with a higher exo content to increase the yield of biperiden (Ia) considerably, especially in combination with the workup described above.

Biperiden (Ia) can then be converted with a pharmacologically acceptable acid in a conventional manner into its acid addition salt. Examples of suitable acids are hydrohalic acids, in particular hydrogen chloride or hydrochloric acid, and organic mono- or dicarboxylic acids such as acetic acid, oxalic acid, maleic acid, fumaric acid, lactic acid, tartaric acid, adipic acid or benzoic acid, also phosphoric acid and sulfuric acid, and the acids mentioned in Fortschritte der Arzneimittelforschung, volume 10, pages 224 et seq., Birkhäuser Verlag, Basle, Stuttgart, 1966. Biperiden (Ia) is normally marketed as hydrochloride.

The exo-1-(bicyclo[2.2.1]hept-5-en-2-yl)ethanone (III-exo) used to prepare the 1-(bicyclo[2.2.1]hept-5-en-2-yl)-3-piperidino-1-propanone (II) is obtained by a Diels-Alder cycloaddition reaction of cyclopentadiene and methyl vinyl ketone. A particularly advantageous method for preparing III, which affords a product with a high content of III-exo, is described in the parallel German patent application 10124452.5, the disclosure of which is incorporated herein by reference.

The cycloaddition of cyclopentadiene and methyl vinyl ketone can in principle be carried out in a solvent conventional for such reactions, such as diethyl ether, benzene, toluene or xylene or else without solvent. It is preferred to use no solvent. Cyclopentadiene and methyl vinyl ketone are normally employed in a molar ratio in the range from 3.0:1 to 0.5:1. They are preferably reacted equimolar or with cyclopentadiene in excess, with the excess preferably being 50 to 150 mol %.

The reaction is usually carried out at temperature in the range from 0 to 60° C., preferably in the range from 10 to 40° C.

Low-boiling constituents, usually unreacted precursors, are usually removed following the cycloaddition by distillation under reduced pressure, preferably under 1 to 150 mbar. The remaining mixture, which consists of about 20% exo- and about 80% endo-1-(bicyclo[2.2.1]hept-5-en-2-yl) ethanone, is reacted with an alkali metal $C_1$–$C_4$-alcoholate. The amount of alkali metal alcoholate is usually from 0.1 to 5% by weight, preferably from 0.2 to 2% by weight, based on the total weight of the mixture. Sodium methanolate is preferably used. The temperature necessary for isomerization of the ethanone III is usually in the range from 50 to 110° C., preferably in the range from 60 to 100° C. For this purpose, the mixture is often heated under reduced pressure to reflux, preferably under a pressure of from 1 to 100 mbar and in particular under a pressure of from 5 to 50 mbar. These conditions are usually applied for from 10 minutes to 5 hours, in particular 20 minutes to 3 hours and specifically 0.5 hours to 2 hours, and then fractional distillation of the resulting mixture is started, preferably distilling out the exo isomer of III. It is assumed that removal of the exo isomer from the equilibrium promotes isomerization of the endo ethanone to the exo form. The fractional distillation normally takes place through a column under reduced pressure, preferably in the range from 1 to 100 mbar, in particular from 1 to 50 and specifically from 1 to 20 mbar. The distillation temperature (distillate temperature) is preferably adjusted to from 50 to 100° C. and specifically to 50 to 80° C. In this way, exo-1-(bicyclo[2.2.1]-hept-5-en-2-yl) ethanone (III-exo) is obtained in a purity which is at least 96%. Redistillation of the distillate results in the exo ethanone III-exo with a purity of up to 100%.

The following example serves to illustrate the invention but is not to be understood as restrictive.

EXAMPLE

1. Preparation of the Starting Material 1.1 exo-1-(Bicyclo[2.2.1]hept-5-en-2-yl)ethanone (III-exo)

198.3 g of cyclopentadiene were rapidly added to 210.3 g of methyl vinyl ketone. After the addition was complete, the solution was stirred at room temperature for one hour and then unreacted precursor was removed by distillation at a temperature of 58° C. and a pressure of 20 mbar. The residue from evaporation, mainly consisting of a mixture of the exo and the endo form of 1-(bicyclo[2.2.1]hept-5-en-2-yl) ethanone (III) in the ratio of 1:4, was heated to reflux with 5 g of sodium methanolate under a pressure of from 10 to 20 mbar for one hour. The reaction mixture was then distilled through a column at a temperature of 75° C. and a pressure of 20 mbar. This resulted in 298.3 g (73% of theory) of exo-1-(bicyclo[2.2.1]hept-5-en-2-yl)ethanone (III-exo) in the form of a pale yellowish oil.

1.2 1-(Bicyclo[2.2.1]hept-5-en-2-yl)-3-piperidino-1-propanone (II)

1.2.1 Preparation of 1-(bicyclo[2.2.1]hept-5-en-2-yl)-3-piperidino-1-propanone (II) using piperidine hydrochloride 510.7 g of exo-1-(bicyclo[2.2.1]hept-5-en-2-yl)ethanone (III-exo), 460.6 g of piperidine hydrochloride and 135.0 g of paraformaldehyde were kept at the reflux temperature in 950 ml of isopropanol for 7 hours. The solvent was removed in a rotary evaporator (pressure: 80 mbar; bath: 60° C.), and the residue was taken up in 1 000 ml of water. The solution was washed three times with 300 ml of diisopropyl ether each time in order to remove unreacted ethanone III. For purification, the washed aqueous solution was mixed with 30 ml of 5M sodium hydroxide solution and 200 ml of diisopropyl ether and stirred for a quarter hour, and the organic phase was separated off. For further purification, the aqueous phase was mixed with 20 ml of 5M sodium hydroxide solution and 200 ml of diisopropyl ether and again stirred for a quarter hour, and the organic phase was separated off. For purification again, the aqueous phase was mixed anew with 20 ml of 5M sodium hydroxide solution and 200 ml of diisopropyl ether and stirred for a quarter hour, and the organic phase was separated off. The remaining, purified aqueous phase was adjusted to pH 7.8 with 105 ml of 50% strength sodium hydroxide solution and extracted with diisopropyl ether. This was done by adding 600 ml of diisopropyl ether, stirring for a quarter hour and separating off the organic phase (1st alkaline extract). The aqueous phase was adjusted to pH 8.2 with a further 60 ml of 5M sodium hydroxide solution and then re-extracted with diisopropyl ether. This was done on this occasion by adding 300 ml of diisopropyl ether, stirring for a quarter hour and separating off the organic phase (2nd alkaline extract). Alkaline extracts 1 and 2 were combined and mixed with 165 ml of water and 35 ml of 5M hydrochloric acid. The mixture was stirred for a quarter hour, the aqueous phase was separated off, and the organic phase was washed with 200 ml of water and evaporated in a rotary evaporator (pressure: down to 10 mbar; bath: 50° C.). The residue obtained from evaporation comprised 473.5 g of an exo/endo mixture of the propanone II in the exo/endo ratio (GC) of 6.4:1 in the form of a pale brown oil; which is 54.1% of theory.

1.2.2 Preparation of 1-(bicyclo[2.2.1]hept-5-en-2-yl)-3-piperidino-1-propanone (II) using piperidinium methanesulfonate 392.1 g of anhydrous methanesulfonic acid were added dropwise to 340.8 g of piperidine in 700 ml of isopropanol while stirring and cooling with water over the course of one hour, during which the temperature rose to 75° C. The dropping funnel was washed with 50 ml of isopropanol, and the mixture was then cooled to 25° C. and stirred at this temperature for half an hour. The precipitated product was filtered off with suction, washed twice with 200 ml of diisopropyl ether each time and dried at 50° C. in vacuo. 688.9 g of piperidinium methanesulfonate were obtained as colorless crystals; which is 95% of theory.

476.7 g of exo-1-(bicyclo[2.2.1]hept-5-en-2-yl)ethanone (III-exo), 761.5 g of piperidinium methanesulfonate and 126.0 g of paraformaldehyde were kept at the reflux temperature in 950 ml of isopropanol for 7 hours. The solvent was removed in a rotary evaporator (pressure: 80 mbar; bath: 60° C.), and the residue was taken up in 1 000 ml of water. The solution was washed three times with 300 ml of diisopropyl ether each time in order to remove unreacted ethanone III. For purification, the washed solution was mixed with 30 ml of 5M sodium hydroxide solution and 200 ml of diisopropyl ether and stirred for a quarter hour, and the organic phase was separated off. For further purification, the aqueous phase was mixed with 20 ml of 5M sodium hydroxide solution and 200 ml of diisopropyl ether and again stirred for a quarter hour, and the organic phase was separated off. For purification again, the aqueous phase was mixed anew with 20 ml of 5M sodium hydroxide solution and 200 ml of diisopropyl ether and stirred for a quarter hour, and the organic phase was separated off. The remaining, purified aqueous phase was adjusted to pH 7.8 with 90 ml of 50% strength sodium hydroxide solution and extracted with diisopropyl ether. This was done by adding 600 ml of diisopropyl ether, stirring for a quarter hour and separating off the organic phase (1st alkaline extract). The aqueous phase was adjusted to pH 8.2 with a further 70 ml of 5M sodium hydroxide solution and then re-extracted with diisopropyl ether. This was done on this occasion by adding 300 ml of diisopropyl ether, stirring for a quarter hour and separating off the organic phase (2nd alkaline extract). Alkaline extracts 1 and 2 were combined and mixed with 165 ml of water and 35 ml of 5M hydrochloric acid. The mixture was stirred for a quarter hour, the aqueous phase was separated off, and the organic phase was washed with 200 ml of water and the solvent was removed in a rotary evaporator (pressure: down to 10 mbar; bath: 50° C.). The residue obtained from evaporation comprised 440.9 g of an exo/endo mixture of the propanone II in the exo/endo ratio (GC) of 22:1 in the form of a pale brown oil; which is 54.0% of theory.

2. Production of biperiden (Ia)

2.1 Production of biperiden using diphenylmagnesium 2.1.1 Production of biperiden using diphenylmagnesium and 1-(bicyclo[2.2.1]hept-5-en-2-yl)-3-piperidino-1-propanone (II) from the reaction described in 1.2.1

800 ml of dioxane were added to 2 000 g of a 25% strength solution of phenylmagnesium chloride in tetrahydrofuran while stirring and cooling slightly over the course of one hour. The temperature rose to 28° C. during this, and a precipitate formed (magnesium chloride-dioxane complex). After addition of dioxane was complete, 387.4 g of an exo/endo mixture of the propanone II obtained as in example 1.2.1 were added over the course of one hour without cooling. The temperature rose to 58° C. during this. The dropping funnel was washed with 30 ml of dioxane, and the mixture was then heated to the reflux temperature and kept at this temperature for one hour. After cooling to 20° C., the mixture was added to 800 g of ice and 600 ml of water while stirring. The mixture was stirred for a quarter hour, during which the temperature rose to 40° C. The organic phase was separated off, and the aqueous phase was extracted twice with 500 ml of diisopropyl ether each time. The organic phases were combined and washed twice with 500 ml of water each time, and the solvent was removed in a rotary evaporator (pressure: down to 10 mbar; bath: 70° C.). The residue from evaporation—532 g of a mixture which consisted essentially of the pair of enantiomers Ia to Id of 1-(bicyclo-[2.2.1]hept-5-en-2-yl)-1-phenyl-3-piperidino-1-propanol (I) in the ratio (GC) 22.3:7.2:2.8:1 (residual content of propanone II in the residue from evaporation: 5.7%)—was dissolved in 4 450 ml of 90% strength isopropanol at 60° C. and, at this temperature, 330 ml of 5M hydrochloric acid were added to the solution. Addition of the acid was followed by stirring at 60° C. for one hour and then at the reflux temperature for half an hour. After cooling to room temperature, the crystals which had separated out were removed and washed twice with 250 ml of isopropanol each time. The moist hydrochloride obtained in this way (320 g; corresponding to 204 g dry) was introduced into 1 175 ml of diisopropyl ether and 350 ml of water and, while stirring, 130 ml of 5M sodium hydroxide solution were added. The mixture was heated to 55° C. and then the aqueous phase was separated off at this temperature, and the diisopropyl ether solution was washed twice with 200 ml of water each time. 530 ml of solvent were removed from the washed diisopropyl ether solution by distillation under atmospheric pressure. The residue from distillation was cooled. After stirring in an ice bath for one hour, the crystals which had separated out were removed, washed with 50 ml of diisopropyl ether and dried at 50° C. in vacuo. 139.0 g of biperiden (Ia) were obtained as colorless crystals of melting point 112 to 114° C. (Ullmanns Enzyklopädie der techn. Chemie, 4th edition, volume 21, Verlag Chemie, 1982, page 627: 112–114° C.); which is 26.9% of theory.

2.1.2 Production of biperiden using diphenylmagnesium and 1-(bicyclo[2.2.1]hept-5-en-2-yl)-3-piperidino-1-propanone (II) from the reaction described in 1.2.2

400 ml of dioxane were added to 1 000 g of a 25% strength solution of phenylmagnesium chloride in tetrahydrofuran while stirring and cooling slightly over the course of one hour. The temperature rose to 27° C. during this, and a precipitate formed (magnesium chloride-dioxane complex). After addition of dioxane was complete, 193.8 g of an exo/endo mixture of the propanone II obtained as in example 1.2.2 were added over the course of one hour without cooling. The temperature rose to 50° C. during this. The dropping funnel was washed with 30 ml of dioxane, and the mixture was then heated to the reflux temperature and kept at this temperature for one hour. After cooling to 15° C., the mixture was added to 400 g of ice and 300 ml of water while stirring. The mixture was stirred for a quarter hour, during which the temperature rose to 38° C. The organic phase was separated off, and the aqueous phase was extracted twice with 250 ml of diisopropyl ether each time.

The organic phases were combined and washed twice with 250 ml of water each time, and the solvent was removed in a rotary evaporator (pressure: down to 10 mbar; bath: 70° C.). The residue from evaporation—254 g of a mixture which consisted essentially of the pair of enantiomers Ia to Id of 1-(bicyclo-[2.2.1]hept-5-en-2-yl)-1-phenyl-3-piperidino-1-propanol (I) in the ratio (GC) 41.4:14.2:2.3 (residual content of propanone II in the residue from evaporation: 7.2%)—was dissolved in 2 225 ml of 90% strength isopropanol at 60° C. and, at this temperature, 170 ml of 5M hydrochloric acid were added to the solution. Addition of the acid was followed by stirring at 60° C. for one hour and then at the reflux temperature for half an hour. After cooling to room temperature, the crystals which had separated out were removed and washed twice with 100 ml of isopropanol each time. The moist hydrochloride obtained in this way (175 g; corresponding to 102.4 g dry) was introduced into 600 ml of diisopropyl ether and 200 ml of water and, while stirring, 70 ml of 5M sodium hydroxide solution were added. The mixture was heated to 55° C. and then the aqueous phase was separated off at this temperature, and the diisopropyl ether solution was washed twice with 100 ml of water each time. 300 ml of solvent were removed from the washed diisopropyl ether solution by distillation under atmospheric pressure. The residue from distillation was cooled. After stirring in an ice bath for one hour, the crystals which had separated out were removed, washed with 30 ml of diisopropyl ether and dried at 50° C. in vacuo. 70.6 g of biperiden (Ia) were obtained as colorless crystals of melting point 112 to 114° C. (Ullmanns Enzyklopädie der techn. Chemie, 4th edition, volume 21, Verlag Chemie, 1982, page 627: 112–114° C.); which is 27.4% of theory.

2.2 Production of biperiden using phenylmagnesium benzyl alcoholate 2.2.1 Production of biperiden using phenylmagnesium benzyl alcoholate and 1-(bicyclo[2.2.1]hept-5-en-2-yl)-3-piperidino-1-propanone (II) from the reaction described in 1.2.1

322 g of dioxane were added to 2 000 g of a 25% strength solution of phenylmagnesium chloride in tetrahydrofuran while stirring and cooling slightly over the course of half an hour. The temperature rose to 27° C. during this, and a precipitate formed (magnesium chloride-dioxane complex). After the addition of dioxane was complete, 197.5 g of benzyl alcohol were added dropwise while cooling at a temperature not exceeding 30° C. over the course of half an hour. Then, without cooling, 387.4 g of an exo/endo mixture of the propanone II obtained as in example 1.2.1 were added over the course of one hour. The temperature rose to 55° C. during this. The mixture was subsequently heated to the reflux temperature and kept at this temperature for one hour. After cooling to 20° C., the mixture was added to 800 g of ice and 600 ml of water with stirring. After stirring for a quarter hour, the organic phase was separated off and the aqueous phase was extracted twice with 500 ml of diisopropyl ether each time. The organic phases were combined and washed twice with 500 ml of water each time, and the solvent was removed in a rotary evaporator (pressure: down to 10 mbar; bath: 70° C.). The residue from evaporation—690 g of a mixture which consisted essentially of the pairs of enantiomers Ia to Id of 1-(bicyclo[2.2.1]hept-5-en-2-yl)-1-phenyl-3-piperidino-1-propanol (I) in the ratio (GC) 18.3:6.0:3.2:1 (residual content of propanone II in the residue for evaporation: 1.1%)—whilst dissolved in 4 450 ml of 90% strength isopropanol at 60° C. and, at this temperature, 310 ml of 5M hydrochloric acid were added to the solution. The addition of acid was followed by stirring at 60° C. for one hour and then at the reflux temperature for half an hour. After cooling to room temperature, the crystals which had separated out were removed and washed twice with 250 ml of isopropanol each time. The moist hydrochloride obtained in this way (398 g; corresponding to 238.8 g dry) was introduced into 1 350 ml of diisopropyl ether and 400 ml of water, and 150 ml of 5M sodium hydroxide solution were added. The mixture was heated to 55° C. and, at this temperature, the aqueous phase was separated off and the diisopropyl ether solution was washed twice with 200 ml of water each time. 600 ml of solvent was removed from the washed diisopropyl ether solution by distillation under atmospheric pressure. The residue from distillation was cooled. After stirring in an ice bath for one hour, the crystals which had separated out were removed, washed with 50 ml of diisopropyl ether and dried at 50° C. in vauo. 161.4 g of biperiden (Ia) were obtained as colorless crystals of melting point 112 to 114° C. (Ullmanns Enzyklopädie der techn. Chemie, 4th edition, volume 21, Verlag Chemie, 1982, page 627: 112–114° C.); which is 31.2% of theory.

2.2.2 Production of biperiden using phenylmagnesium benzyl alcoholate and 1-(bicyclo[2.2.1]hept-5-en-2-yl)-3-piperidino-1-propanone (II) from the reaction described in 1.2.2

322 g of dioxane were added to 2 000 g of a 25% strength solution of phenylmagnesium chloride in tetrahydrofuran while stirring and cooling slightly over the course of half an hour. The temperature rose to 27° C. during this, and a precipitate formed (magnesium chloride-dioxane complex). After the addition of dioxane was complete, 197.5 g of benzyl alcohol were added dropwise while cooling at a temperature not exceeding 30° C. over the course of half an hour. Then, without cooling, 387.4 g of an exo/endo mixture of the propanone II obtained as in example 1.2.2 were added over the course of one hour. The temperature rose to 55° C. during this. The mixture was subsequently heated to the reflux temperature and kept at this temperature for one hour. After cooling to 20° C., the mixture was added to 800 g of ice and 600 ml of water with stirring. After stirring for a quarter hour, the organic phase was separated off and the aqueous phase was extracted twice with 500 ml of diisopropyl ether each time. The organic phases were combined and washed twice with 500 ml of water each time, and the solvent was removed in a rotary evaporator (pressure: down to 10 mbar; bath: 70° C.). The residue from evaporation—682.8 g of a mixture which consisted essentially of the pairs of enantiomers Ia to Id of 1-(bicyclo-[2.2.1]hept-5-en-2-yl)-1-phenyl-3-piperidino-1-propanol (I) in the ratio (GC) 47.0:15.1:3.6:1 (residual content of propanone II in the residue for evaporation: 0.8%—whilst dissolved in 4 450 ml of 90% strength isopropanol at 60° C. and, at this temperature, 310 ml of 5M hydrochloric acid were added to the solution. The addition of acid was followed by stirring at 60° C. for one hour and then at the reflux temperature for half an hour. After cooling to room temperature, the crystals which had separated out were removed and washed twice with 250 ml of isopropanol each time. The moist hydrochloride obtained in this way (400 g; corresponding to 216.6 g dry) was introduced into 1 350 ml of diisopropyl ether and 400 ml of water, and 150 ml of 5M sodium hydroxide solution were added. The mixture was heated to 55° C. and, at this temperature, the aqueous phase was separated off and the diisopropyl ether solution was washed twice with 200 ml of water each time. 600 ml of solvent was removed from the washed diisopropyl ether solution by distillation under atmospheric pressure. The residue from distillation was cooled. After stirring in an ice bath for one hour, the crystals which had separated out were removed, washed with 50 ml of diisopropyl ether and dried at 50° C. in vacuo. 161.4 g of biperiden (Ia) were obtained as colorless crystals of melting point 112 to 114° C. (Ullmanns Enzyklopädie der techn. Chemie, 4th edition, volume 21, Verlag Chemie, 1982, page 627: 112–114° C.); which is 29.1% of theory.

3. Production of biperiden hydrochloride 93.4 g biperiden (Ia) were dissolved in 1 000 ml of isopropanol by heating to the reflux temperature. The solution was filtered hot and the filter was washed with 100 ml of isopropanol. 65 ml of 5M hydrochloric acid were added to the combined filtrates at 75° C. The mixture was then heated to reflux for 15 minutes. After cooling to room temperature it was stirred for one hour, and the precipitated solid was filtered off with suction, washed twice with 50 ml of isopropanol each time and dried at 70° C. in vacuo. 103.2 g of biperiden hydrochloride were obtained in the form of colorless crystals of melting point 278 to 280° C. (Ullmanns Enzyklopädie der techn. Chemie, 4th edition, volume 21, Verlag Chemie, 1982, page 627: 278–280° C.); which is 98.9% of theory.

We claim:

1. A method for the production of biperiden by reacting an exo/endo mixture of 1-(bicyclo[2.2.1]hept-5-en-2-yl)-3-piperidino-1-propanone with an exo/endo ratio of at least 4.5:1 with a phenylmagnesium compound, characterized in that the production of the exo/endo mixture of 1-(bicyclo-(2.2.1]hept-5-en-2-yl)-3-piperidino-1-propanone comprises the following steps:

a) reaction of exo-1-(bicyclo[2.2.1]hept-5-en-2-yl) ethanone with a formaldehyde source and an acid addition salt of piperidine or with a formaldehyde source and piperidine in the presence of an acid in an organic solvent or in a mixture thereof with water, b) conversion of the resulting reaction mixture into an aqueous solution and extraction of this aqueous solution with an organic solvent which has limited miscibility or is immiscible with water at a pH not exceeding 7, c) extraction of the aqueous raffinate obtained in b), which contains the exo/endo mixture of 1-(bicyclo[2.2.1]hept-5-en-2-yl)-3-piperidino-1-propanone, at a pH of at least 7.5 with an organic solvent which has limited miscibility or is immiscible with water, and d) removal of the organic extract, purification of the organic extract by extraction with acid and subsequent removal of the solvent, resulting in 1-(bicyclo-[2.2.1] hept-5-en-2-yl)-3-piperidino-1-propanone with an exo/endo ratio of at least 4.5:1.

2. The method of claim 1, characterized in that an organic sulfonic acid of the general formula $RSO_3H$ in which R is $C_1$–$C_4$-alkyl, phenyl or $C_1$–$C_4$-alkyl-substituted phenyl is used as the acid in step a).

3. The method of claim 2, characterized in that methanesulfonic acid is employed.

4. The method of claim 3, characterized in that piperidinium methanesulfonate is employed as the acid addition salt of piperidine in step a).

5. The method of claim 1, characterized in that piperidine hydrochloride or piperidine in the presence of hydrochloric acid or hydrogen chloride is employed in step a).

6. The method of claim 1, characterized in that the molar ratio of exo-1-(bicyclo-(2.2.1]hept-5-en-2-yl)ethanone and piperidine or its acid addition salt in step a) is in the range from 1:0.9 to 1:2.

7. The method of claim 1, characterized in that the formaldehyde source is employed in step a) in an excess of from 10 to 100 mol % relative to the exo-1-(bicyclo[2.2.1] hept-5-en-2-yl)ethanone.

8. The method of claim 1, characterized in that after removal of the organic solvent in step b) the reaction mixture from step a) is converted into an aqueous solution, firstly extracted with an organic solvent of limited or zero miscibility with water, the pH of the aqueous raffinate is adjusted to a value not exceeding 7 by adding a base or a basic aqueous solution, where the total amount of base used is from 5 to 15 mol % of the amount of exo-1-(bicyclo[2.2.1] hept-5-en-2-yl)ethanone used in step a), and again extracted with an organic solvent of limited or zero miscibility with water.

9. The method of claim 1, characterized in that the pH is adjusted in step c) to a value in the range from 8.0 to 8.5.

10. The method of claim 1, characterized in that a mineral acid is used in step d) for extraction with acid.

11. The method of claim 10, characterized in that the acid is employed in an amount of from 0.02 to 0.1 proton equivalents based on the amount of exo-1-(bicyclo[2.2.1]-hept-5-en-2-yl)ethanone employed in step a).

12. The method of claim 1, characterized in that paraformaldehyde is used as the formaldehyde source in step a).

13. The method of claim 1, characterized in that diphenylmagnesium or a phenylmagnesium compound of the general formula

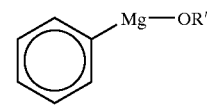

where R' is $C_1$–$C_4$-alkyl, $C_4$–$C_6$-cycloalkyl, $C_4$–$C_6$-cycloalkyl-$C_1$–$C_4$-alkyl, phenyl-$C_1$–$C_4$-alkyl, substituted phenyl-$C_1$–$C_4$-alkyl, heteroaryl, heteroaryl-$C_1$–$C_4$-alkyl or benzhydryl, is used as the phenylmagnesium compound.

14. The method as of claim 1, characterized in that the isolation of biperiden from the mixture of isomers of the 1-(bicyclo[2.2.1]hept-5-en-2-yl)-1-phenyl-3-piperidino-1-propanol formed in the reaction of the exo/endo, mixture of 1-(bicyclo[2.2.1]hept-5-en-2-yl)-3-piperidino-1-propanone with the phenylmagnesium compound comprises the following steps:

reaction of the mixture of isomers with HCl in a mixture of water and a polar organic solvent of limited or infinite miscibility with water, and isolation of the hydrochloride formed thereby, reaction of the hydrochloride in a mixture of water and at least one polar dialkyl ether having limited or zero miscibility with water and having 4 to 8 C atoms with a base, separation of the two phases which have formed at elevated temperature, evaporation of part of the ether from the organic phase and crystallization of the biperiden by cooling.

15. 1-(Bicyclo[2.2.1]hept-5-en-2-yl)-1-phenyl-3-piperidino-1-propanone having an exo/endo ratio of at least 4.5:1.

* * * * *